United States Patent [19]

Cragoe, Jr. et al.

[11] 4,092,414
[45] May 30, 1978

[54] 3,4-DIHYDROSPIRO-2H-1,3-BENZOXAZINES AND THEIR USE IN TREATING EDEMA, ABNORMAL ELECTROLYTE RETENTION, AND INFLAMMATION

[75] Inventors: Edward J. Cragoe, Jr., Lansdale; Everett M. Schultz, Ambler; Gerald E. Stokker, Gwynedd Valley, all of Pa.

[73] Assignee: Merck & Co., Inc., Rahway, N.J.

[21] Appl. No.: 659,442

[22] Filed: Feb. 19, 1976

Related U.S. Application Data

[63] Continuation-in-part of Ser. No. 571,462, Apr. 25, 1975, abandoned.

[51] Int. Cl.² .................. A01N 9/00; A01N 9/22; C07D 265/00; C07D 273/00
[52] U.S. Cl. .................. 424/248.51; 424/248.4; 424/248.52; 424/248.57; 544/70
[58] Field of Search ............ 260/244; 424/248, 248.4, 424/248.52, 248.57, 248.51; 544/70

[56] References Cited

U.S. PATENT DOCUMENTS

| | | | |
|---|---|---|---|
| 3,794,734 | 2/1974 | Cragoe et al. | 424/330 |
| 3,798,218 | 3/1974 | Fauran et al. | 260/246 |
| 3,809,721 | 5/1974 | Schultz et al. | 260/570.9 |
| 3,887,550 | 6/1975 | Beckwith | 260/244 R |

OTHER PUBLICATIONS

J. Org. Chem. 33 (1) 1–8 (1968) McDonagh et al. "Ring-Chain Tautomerism of Derivatives . . . Ketones".
Chem. Abst. 72, 111394(n) (1970) Shira: et al. "Phenoxazine related compounds".

*Primary Examiner*—Albert T. Meyers
*Assistant Examiner*—D. W. Robinson
*Attorney, Agent, or Firm*—Mario A. Monaco; Raymond M. Speer

[57] ABSTRACT

3,4-Dihydrospiro-2H-1,3-benzoxazines are prepared by condensing aminomethylphenols with cyclic ketones. The products are diuretic and anti-inflammatory agents, and are useful in the treatment of autoimmune diseases, such as multiple sclerosis.

12 Claims, No Drawings

3,4-DIHYDROSPIRO-2H-1,3-BENZOXAZINES AND THEIR USE IN TREATING EDEMA, ABNORMAL ELECTROLYTE RETENTION, AND INFLAMMATION

This application is a continuation-in-part of copending application Ser. No. 571,462, filed Apr. 25, 1975, and now abandoned.

This invention is concerned with novel 3,4-dihydrospiro-2H-1,3-benzoxazines having therapeutic utility, processes for their preparation, methods of treating inflammation, edema and autoimmune diseases, and novel pharmaceutical formulations comprising at least one of the novel compounds as active ingredient.

One embodiment of this invention is particularly concerned with the novel compounds of structural formula:

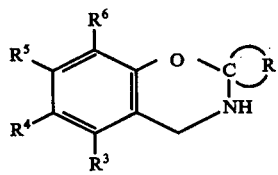

wherein
$R^3$ is
 (1) hydrogen,
 (2) methyl,
 (3) chloro, or
 (4) methoxy;
$R^4$ is
 (1) halo, such as chloro, bromo, or iodo,
 (2) lower alkyl, especially $C_{1-7}$ alkyl, either straight or branched chain, such as methyl, propyl, isopropyl, butyl, t-butyl, sec-butyl, pentyl, isopentyl, hexyl, or heptyl,
 (3) adamantyl;
$R^5$ is
 (1) hydrogen,
 (2) lower alkyl, especially $C_{1-7}$ alkyl, either straight or branched chain,
 (3) lower alkoxy, especially $C_{1-5}$ alkoxy, either straight or branched chain such as methoxy, ethoxy, propoxy, butoxy or pentoxy, or
 (4) halo, such as fluoro, chloro, bromo, or iodo;
$R^6$ is
 (1) halo, such as chloro, bromo or iodo;
 (2) lower alkyl, especially $C_{1-7}$ alkyl, either straight or branched chain,
 (3) lower alkylthio, especially $C_{1-3}$ alkylthio, or
 (4) trifluoromethyl;
$R^5$ and $R^6$ taken together is —N=CH—CH=CH—;
$\bigcirc R$ is
 (1) a spiro-carbocycle of 5,6 or 10–17 members, either unsubstituted or substituted with
  (a) lower alkyl, especially $C_{1-7}$ alkyl,
  (b) lower alkoxy, especially $C_{1-5}$ alkoxy,
  (c) phenyl, either unsubstituted or substituted with lower alkoxy, especially $C_{1-5}$ alkoxy,
  (d) lower alkanoyloxy, especially $C_{2-5}$-alkanoyloxy;
 (2) a 6-membered spiro-heterocycle containing 1 or 2 hetero atoms selected from oxygen, sulfur and nitrogen such as spiro-tetrahydropyran, spiro-tetrahydrothiapyran, spiro-3,5-dithiacyclohexane, spiro-piperidine, wherein the nitrogen heteroatom can be substituted with (a) lower alkyl, especially $C_{1-7}$ alkyl,
 (b) phenyl-lower alkyl, especially phenyl-$C_{1-3}$ alkyl,
 (c) lower alkanoyl, especially $C_{2-5}$ alkanoyl,
(3) spiro-polycycloalkyl of 6–15 members such as spiro-nortricyclane, or spiro-adamantane, or

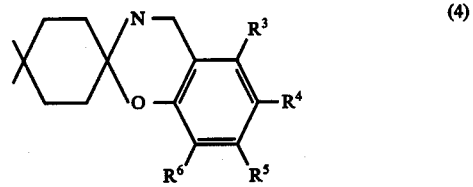

wherein $R^3$, $R^4$, $R^5$, and $R^6$ are as previously defined.

A preferred aspect of the novel compounds of this invention are those of Formula I, wherein $R^3$ and $R^5$ are both hydrogen.

A more preferred aspect of the novel compounds of this invention are those of Formula I, wherein $R^3$ and $R^5$ are hydrogen, $R^4$ is $C_{1-7}$ alkyl, and $R^6$ is halo.

An even more preferred aspect of the novel compounds of this invention are those of Formula I, wherein $R^3$ and $R^5$ are hydrogen, $R^4$ is $C_{1-7}$ alkyl, particularly branched alkyl such as t-butyl, $R^6$ is halo and $\bigcirc R$ is spiro-tetrahydrothiapyran or spiro-cyclohexane.

Another embodiment of this invention is the process for the preparation of the novel compounds of Formula I which is represented by:

REACTION SCHEME I

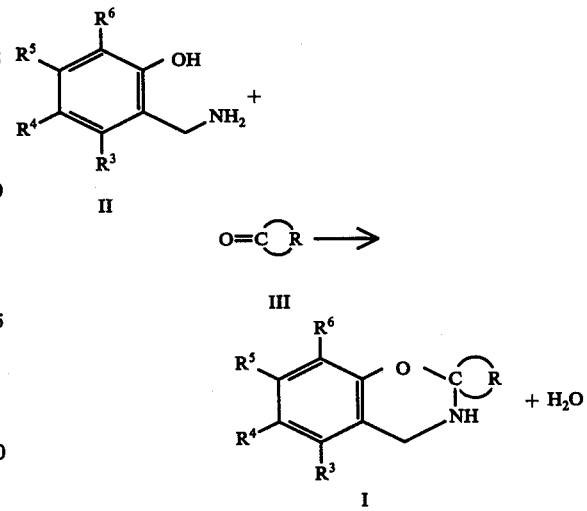

This novel process comprises mixing approximately equimolar amounts of an o-hydroxybenzylamine of Formula II and a cyclic ketone of Formula III in an inert organic solvent such as benzene, dioxan, tetrahydrofuran, or the like, and warming the reaction mixture to temperatures of from 20°–110° C. or reflux temperature.

It is sometimes advantageous to perform the condensation reaction in the presence of an acid catalyst such as a sulfonic acid such as p-toluenesulfonic acid or methanesulfonic acid, or a $C_{1-5}$ alkanoic acid, preferably acetic acid. The amount of acid is not critical but it is preferred to use only a catalytic amount.

It is also sometimes advantageous to remove the water produced during the condensation from the reaction environment by having present an otherwise inert dehydrating agent such as molecular sieves, sodium sulfate, magnesium sulfate, or the like, or by refluxing the mixture under a Dean-Stark water trap where the solvent forms an azeotrope with water. Isolation of the product from the reaction mixture is performed by routine techniques well within the skill of one skilled in the art. Generally, the mixture is washed with a dilute base if an acid catalyst has been used. This is followed by a water wash, drying, evaporation of the solvent, and recrystallization from a solvent such as ethanol. If no acid catalyst is used, the reaction mixture is evaporated to dryness directly and the residue is purified by crystallization.

The o-hydroxybenzylamines of Structure II, used as starting materials in the novel process of this invention, are generally known compounds and readily prepared by processes described in the literature such as U.S. Pat. Nos. 3,794,734; 3,809,721; and 3,864,401; and Great Britain Patent No. 1,374,294.

Further embodiments of this invention are the novel pharmaceutical compositions comprising the spiro-benzoxazines as active ingredient, and the novel methods of treating edema, inflammation, and autoimmune diseases such as multiple sclerosis with the pharmaceutical compositions.

Pharmacological studies employing rats and dogs as the experimental animals indicate that the instant products and compositions containing the active products are effective diuretic and saluretic agents which can be used in the treatment of conditions associated with electrolyte and fluid retention. When administered in therapeutic dosages in conventional vehicles, the instant products effectively reduce the amount of sodium and chloride ions in the body, lower dangerous excesses of fluid level to acceptable levels and, in general, alleviate conditions usually associated with edema. Further, studies employing the mouse ear test and the carrageenan edema test indicate that these compounds are effective anti-inflammatory agents useful both topically and systemically. Other studies have shown that the novel compounds of this invention inhibit experimental allergic encephalomyelitis in rats indicating their utility in the treatment of autoimmune diseases, such as multiple sclerosis.

The compositions containing the spiro-benzoxazines of this invention as the active ingredient for use as diuretic, saluretic, anti-inflammatory agents, or in the treatment of autoimmune diseases can be administered in a wide variety of therapeutic dosage forms in conventional vehicles for systemic administration as, for example, by oral administration in the form of tablets, capsules, solutions, or suspensions, or by intravenous injection. The daily dosage of the products may be varied over a wide range varying from 50 to 2,000 mg. The compositions are preferably provided in the form of scored tablets containing 5, 10, 25, 50, 100, 150, 250, and 500 milligrams of the active ingredient for the symptomatic adjustment of the dosage to the patient to be treated. An effective amount of the drug is ordinarily supplied at a dosage level of from about 1 mg. to about 50 mg./kg. of body weight per day. Preferably the range is from about 1 mg. to 7 mg./kg. of body weight per day. These dosages are well below the toxic or lethal dose of the products. Capsules containing the products of this invention can be prepared by mixing a spiro-benzoxazine of this invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. The liquid forms in which the active ingredients may be incorporated include suitably flavored suspending or dispersing agents such as the synthetic and natural gums, for example, tragacanth, acacia, methylcellulose and the like. Other dispersing agents which may be employed include glycerin and the like. For parenteral administration sterile suspensions and solutions are desired. Isotonic preparations which generally contain suitable preservative are employed when intravenous administration is desired.

The compositions containing the spiro-benzoxazines as the active ingredient useful as topical anti-inflammatory agents are effective in topical treatment of dermatological disorders and the like conditions, such as dermatitis (actinic, atopic, contact, eczematoid, seborrheic and stasis), dermatitis herpetiformis, lichen planus, neurodermatitis, intertrigo, lichen simplex chronicus, pruritus and psoriasis, as well as for topical treatment of inflammations of the respiratory and intestinal mucosa such as allergic rhinitis, bronchitis, bronchial asthma, bronchiectasis, colitis, and the like. The spiro-benzoxazines are ordinarily administered in the form of a pharmaceutical composition comprising the active compound in combination with a pharmacologically acceptable carrier adapted for topical administration. These topical pharmaceutical compositions may be in the form of a cream, ointment, gel or aerosol formulation adapted for application to the skin for treatment of dermatoses; or it may be in the form of a solution, suspension or aerosol adapted for topical spray application to respiratory passages for treatment of nasal allergies, bronchial inflammations, and the like; or in the form of suppositories or enclosed in enteric capsules for treatment of intestinal inflammations. For treatment of dermatological disorders, these topical pharmaceutical compositions containing the spiro-benzoxazines ordinarily include about 0.1% to 15%, preferably about 5%, of the active compound, in admixture with about 95% of vehicle.

EXAMPLE 1

3,4-Dihydro-6-(1,1-dimethylethyl)-8-iodospiro[2H-1,3-benzoxazine-2,4'-tetrahydrothiopyran]

A mixture of 2-aminomethyl-4-(1,1-dimethylethyl)-6-iodophenol (3.0 g., 0.01 mole), tetrahydrothiopyran-4-one (1.18 g., 0.01 mole), and benzene (100 ml.), is refluxed under a Dean-Stark trap for 4 hr. The solvent is evaporated, and the residue is crystallized from ethanol to obtain 3,4-dihydro-6-(1,1-dimethylethyl)-8-iodospiro-[2H-1,3-benzoxazine-2,4'-tetrahydrothiopyran], (2.5 g.), m.p. 123°–124° C.

Following the procedure substantially as described in Example 1, but substituting for the 2-aminomethyl-4-(1,1-dimethylethyl)-6-iodophenol and tetrahydrothiopyran-4-one used therein, equimolar amounts of compounds of Formula II and of Formula III, respectively, identified in Table I, there are produced the products of Formula I, also identified in Table I, in accordance with Reaction Scheme I.

TABLE I
| $R^3$ | $R^4$ | $R^5$ | $R^6$ | O=C⟨R | m.p. (° C.) |
|---|---|---|---|---|---|
| H— | $(CH_3)_3C$— | H— | I— | 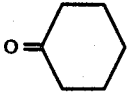 | 100–101 |
| H | $(CH_3)_3C$— | H | Cl— | 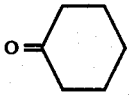 | 107–108 |
| H | $(CH_3)_3C$— | H | I— | 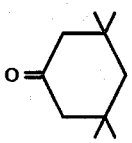 | 171–172 |
| H | $(CH_3)_3C$— | H | I— | 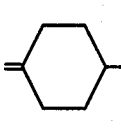 | 108–109 |
| Cl | Cl | H | Cl | 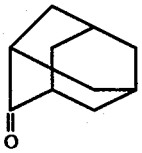 | 171.5–172.5 |
| $CH_3$ | Cl— | $C_2H_5$— | Cl | 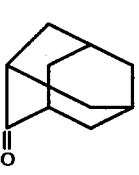 | |
| $CH_3$ | Br | $CH_3$ | Br | 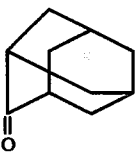 | |
| H | $(CH_3)_3C$— | H | I | 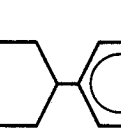 | |
| H | $(CH_3)_3C$— | H | I | 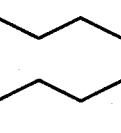 | |
| H | $(CH_3)_3C$— | H | I | 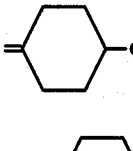 | |
| H | $(CH_3)_3C$— | H | I | 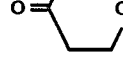 | |

TABLE I-continued

| $R^3$ | $R^4$ | $R^5$ | $R^6$ | O=C⟨R | m.p. (° C.) |
|---|---|---|---|---|---|
| H | (CH₃)₃C— | H | I | 1,3-dithian-2-ylidene (O=C with -S-CH₂-CH₂-CH₂-S- ring) | |

EXAMPLE 2

3,4-Dihydro-6-(1,1-dimethylethyl)-8-iodo-1'-methyl-spiro-[2H-1,3-benzoxazin-2,4'-piperidine]

A mixture of 2-aminomethyl-4-(1,1-dimethylethyl)-6-iodophenol (6.0 g., 0.02 mole), 1-methyl-4-piperidone (2.24 g., 0.02 mole), acetic acid (2 ml.) and benzene (100 ml.) is refluxed under a Dean-Stark trap for 4 hrs. The clear yellow solution then is washed with 2% sodium hydroxide solution, water and salt brine and dried (MgSO₄). The residue that remains after evaporation of the benzene is crystallized from ethanol to obtain 3,4-dihydro-6-(1,1-dimethylethyl)-8-iodo-1'-methyl-spiro[2H-1,3-benzoxazin-2,4'-piperidine], (4.6 g.), m.p. 155°–156.5° C.

Following the procedure substantially as described in Example 2, but substituting for the 2-aminomethyl-4-(1,1-dimethylethyl)-6-iodophenol and 1-methyl-4-piperidone used therein, equimolar amounts of compounds of Formula II and of Formula III respectively, identified in Table II, there are produced the products of Formula I, also identified in Table II, in accordance with Reaction Scheme I.

TABLE II

| $R^3$ | $R^4$ | $R^5$ | $R^6$ | O=C⟨R | m.p. (° C.) |
|---|---|---|---|---|---|
| H | (CH₃)₃C— | H | Cl | 1-methyl-4-piperidone (O=C piperidine ring with N—CH₃) | 135–137 |
| H | (CH₃)₃C— | H | I | bicyclic ketone | 141–142 |
| H | (CH₃)₃C— | H | I | cyclododecanone | 135–136.5 |
| H | (CH₃)₃C— | H | I | 1-(2-phenylethyl)-4-piperidone (piperidine with N—(CH₂)₂—C₆H₅) | 138–139 |
| H | (CH₃)₃C— | H | I | 2-adamantanone | 165–166 |
| CH₃— | CH₃— | CH₃— | CH₃— | cyclohexanone | 117–119 |
| CH₃— | Cl— | CH₃— | Cl | cyclohexanone | 98–100 |
| H | (CH₃)₃C— | H | I | 1-acetyl-4-piperidone (piperidine with N—COCH₃) | 155–160 |
| H | (CH₃)₃C— | H | I | 4-acetoxycyclohexanone (cyclohexanone with —OCCH₃ (O=)) | Glass |

TABLE II-continued

| R³ | R⁴ | R⁵ | R⁶ | O=C˂R | m.p. (° C.) |
|---|---|---|---|---|---|
| OCH₃ | Cl | OCH₃ | Cl | 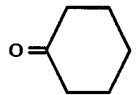 | 99–100 |

EXAMPLE 3

3,4-Dihydro-6-(1,1-dimethylethyl)-8-trifluoromethyl-spiro-[2H-1,3-benzoxazine-2,2'-tricyclo(3.3.1.1³,⁷)decane]

Step A: Preparation of 2-trifluoromethyl-4-(1,1-dimethylethyl)phenol

A mixture of 2-trifluoromethylphenol (25 g., 0.15 moles), tert-butyl alcohol (12 g., 0.16 mole), trifluoroacetic acid (100 ml.) and 96% sulfuric acid (2 ml.) is stirred at about 20° C. for 48 hours. The mixture then is evaporated as far as possible under reduced pressure at 35°–40° C. The residue is dissolved in benzene (500 ml.) and the solution is washed with water, saturated NaHCO₃ solution and saturated salt brine and dried over anhydrous MgSO₄. The dried solution is again evaporated under reduced pressure and the temperature is finally raised to 140°–145° C. under 65 mm. pressure to remove unchanged 2-trifluoromethylphenol. The residue is distilled at 65 mm. after collecting a small forerun (75% unchanged starting phenol and 25% product), 2-trifluoromethyl-4-(1,1-dimethylethyl)phenol (13.6 g.) is collected at 120°–132° C. as a pale pink oil that is 98% pure by gas liquid chromatography analysis and can be used directly in the next step.

Step B: Preparation of 2-aminomethyl-4-(1,1-dimethylethyl)-6-trifluoromethylphenol 2-Trifluoromethyl-4-(1,1-dimethylethyl)phenol (15.6 g., 0.062 mole) is dissolved in a mixture of glacial acetic acid (200 ml.) and 96% sulfuric acid (150 ml.). The mixture is stirred and finely powdered N-hydroxymethyl-2-chloroacetamide (8 g., 0.065 mole) is added in small portions at 20°–25° C. Stirring then is continued for 5 hours after which the mixture is poured into water (3 l.). The 2-(2-chloroacetamidomethyl)-4-(1,1-dimethylethyl)-6-trifluoromethylphenol that separates is collected and dried by suction to obtain a solid (19 g., m.p. about 85°–100° C.).

The solid, the 2-chloroacetyl derivative of 2-aminomethyl-4-(1,1-dimethylethyl)-6-trifluoromethylphenol is dissolved in a mixture of ethanol (75 ml.) and 12 N hydrochloric acid (25 ml.). The mixture is refluxed for 5 hours, cooled to 20° C. and diluted with 12 N hydrochloric acid (150 ml.). Upon cooling to −20° C., the product separates (14 g.). It is crystallized from ethanol-12 N hydrochloric acid (1:4) to obtain pure 2-aminomethyl-4-tertbutyl-6-trifluoromethylphenol hydrochloride, m.p. 202°–204° C. This material is added to 500 ml. of warm water and treated with excess ammonium hydroxide. The precipitate is collected, washed with water, and air dried to give the free base, m.p. about 148° C.

Step C: Preparation of 3,4-dihydro-6-(1,1-dimethylethyl)-8-trifluoromethylspiro[2H-1,3-benzoxazine-2,2'-tricyclo(3.3.1.1³,⁷)decane]

A solution of 2-aminomethyl-4-(2,2-dimethylethyl)-6-trifluoromethylphenol (1.24 g., 0.005 mole), 2-oxotricyclo(3.3.1.1³,⁷)decane (0.75 g., 0.005 mole) and acetic acid (0.25 ml.) in dry benzene (50 ml.) is refluxed under a constant water separator for 3 hr. The solution is cooled, washed with 2% sodium hydroxide solution, water and salt brine and then dried (MgSO₄) and evaporated under reduced pressure. The solid residue (1.2 g.) is crystallized from hexane to obtain 3,4-dihydro-6-(1,1-dimethylethyl)-8-trifluoromethylspiro[2H-1,3-benzoxazine-2,2'-tricyclo(3.3.1.1³,⁷)decane] (0.65 g.), m.p. 125°–126.5° C.

EXAMPLE 4

3,4-Dihydro-6-(1,1-dimethylethyl)-8-(methylthio)-spiro[2H-1,3-benzoxazine-2,2'-tricyclo(3.3.1.1³,⁷)decane]

Step A: Preparation of 2-(methylthio)-4-(1,1-dimethylethyl)phenol

A mixture of 37.5 g. (0.25 mole) of 4-(1,1-dimethylethyl)phenol, 50 ml. of 70% perchloric acid and 40 ml. of phosphorus oxychloride was cooled to 0° C. and treated with 18.0 ml., (19.5 g., 0.25 mole) of dimethyl sulfoxide dropwise with vigorous stirring. Stirring was continued at 0° C. for 2 hours, and room temperature for 16 hours. The mixture was poured onto ice. The precipitate was collected on a filter, washed with ice-water, sucked dry, and washed with ether. The filter cake was added to 500 ml. of saturated potassium chloride solution and refluxed 4 hours. After standing at room temperature overnight, the oily product was extracted into ether, washed with water, saturated sodium chloride solution, dried, and evaporated to dryness to give 42 g. of 2-(methylthio)-4-(1,1-dimethylethyl)phenol.

Step B: Preparation of 2-aminomethyl-4-(1,1-dimethylethyl)-6-(methylthio)phenol

A cold solution of (5.3 g., 0.027 mole) of the phenol from Step A, in 150 ml. of acetic acid and 10 ml. of sulfuric acid was treated with 3.32 g. (0.027 mole) of N-hydroxymethyl-2-chloroacetamide portionwise over about 15 minutes and was stirred for 16 hours at room temperature. The mixture was poured into 1 liter of cold water. The precipitated gum was extracted into ether and washed three times with water and saturated sodium chloride solution and evaporated to dryness. The residue was refluxed with 30 ml. of ethanol and 15 ml. of hydrochloric acid for 4 hours. The mixture was evaporated to dryness and the residue was triturated with ether, collected and recrystallized from a mixture of 10 ml. of ethanol and 12 ml. of ether to give 3.5 g. of the hydrochloride salt of the product; m.p. 179°–181° C.

This salt was added to 100 ml. of water and treated with excess ammonium hydroxide to give 2-aminomethyl-4-(1,1-dimethylethyl)-6-methylthiophenol, m.p. 127°–131° C.

Step C: Preparation of 3,4-dihydro-6-(1,1-dimethylethyl)-8-(methylthio)spiro[2H-1,3-benzoxazine-2,2'-tricyclo(3.3.1.1³,⁷)decane]

Employing the procedure of Example 3, Step C, but substituting for the 2-aminomethyl-4-(1,1-dimethylethyl)-6-trifluoromethylphenol used therein, an equimolar amount of 2-aminomethyl-4-(1,1-dimethylethyl)-6-(methylthio)phenol, there is produced 3,4-dihydro-6-(1,1-dimethylethyl)-8-(methylthio)spiro[2H-1,3-benzoxazine-2,2'-tricyclo(3.3.1.1$^{3,7}$)decane], m.p. 162°–164° C.

EXAMPLE 5

3,4-Dihydro-6,8-diiodospiro[2H-1,3-benzoxazine-2,2'-tricyclo(3.3.1.1$^{3,7}$)decane]

Step A: Preparation of 2-aminomethyl-4,6-diodophenol

Iodine monochloride (4.95 g., 0.03 mole) was added rapidly to a stirred solution of 1.6 g. (0.013 mole) of 2-aminomethylphenol in 100 ml. of water and 1.5 ml. of hydrochloric acid. After 2½ hours at room temperature, the mixture was cooled to −10° C. and filtered. The filter cake was washed with water and concentrated hydrochloric acid and recrystallized from a mixture of 40 ml. of 95% ethanol, 50 ml. of water, and 4 ml. of hydrochloric acid to give 4.5 g. of the hydrochloride salt, m.p. 215°–216° C.

Solution in about 500 ml. of water and addition of excess ammonium hydroxide provided 2-aminomethyl-4,6-diodophenol.

Step B: Preparation of 3,4-dihydro-6,8-diiodospiro[2H-1,3-benzoxazine-2,2'-tricyclo(3.3.1.1$^{3,7}$)decane]

Employing the procedure of Example 3, Step C, but substituting for the 2-aminomethyl-4-(1,1-dimethylethyl)-6-trifluoromethylphenol used therein, an equimolar amount of 2-aminomethyl-4,6-diodophenol, there is produced 3,4-dihydro-6,8-diiodospiro[2H-1,3-benzoxazine-2,2'-tricyclo(3.3.1.1$^{3,7}$)decane].

EXAMPLE 6

3,4-Dihydro-6-(1-methylethyl)-8-iodospiro[2H-1,3-benzoxazine-2,2'-tricyclo(3.3.1.1$^{3,7}$)decane]

Step A: Preparation of 2-iodo-4-(1-methylethyl)phenol

A solution of 27.2 g. (0.20 mole) of 4-(1-methylethyl)phenol in 100 ml. of acetic acid was stirred vigorously while 32.5 g. (0.20 mole) of iodine monochloride in 50 ml. of acetic acid was added slowly. The mixture was refluxed for 6 hours, cooled, and poured into 1 liter of water containing a little sodium bisulfite. The crude oily product that separated was extracted into ether and washed well with water and saturated sodium chloride solution, dried and concentrated to dryness. The residue was distilled under reduced pressure to give 26.1 g. of 2-iodo-4-(1-methylethyl)phenol, b.p. 137°–140° C./15 mm Hg.

Step B: Preparation of 2-aminomethyl-4-(1-methylethyl)-6-iodophenol

Employing the procedure of Example 4, Step B, but substituting for the 2-methylthio-4-(1,1-dimethylethyl)-phenol, an equimolar amount of 2-iodo-4-(1-methylethyl)phenol, there is produced 2-aminomethyl-4-(1-methylethyl)-6-iodophenol hydrochloride, m.p. 211°–212° C., and the free base thereof.

Step C: Preparation of 3,4-dihydro-6-(1-methylethyl)-8-iodospiro[2H-1,3-benzoxazine-2,2'-tricyclo(3.3.1.1$^{3,7}$)-decane]

Employing the procedure of Example 3, Step C, but substituting for the 2-aminomethyl-4-(1,1-dimethylethyl)-6-trifluoromethylphenol used therein, an equimolar amount of 2-aminomethyl-4-(1-methylethyl)-6-iodophenol, there is produced 3,4-dihydro-6-(1-methylethyl)-8-iodospiro[2H-1,3-benzoxazine-2,2'-tricyclo(3.3.1.1$^{3,7}$)decane].

EXAMPLE 7

3,4-Dihydro-6-[1-tricyclo(3.3.1.1$^{3,7}$)decyl]-8-iodospiro[2H-1,3-benzoxazine-2,2'-tricyclo(3.3.1.1$^{3,7}$)decane]

Step A: Preparation of 2-aminomethyl-4-[1-tricyclo(3.3.1.1$^{3,7}$)decyl]phenol hydrochloride N-hydroxymethyl-2-chloroacetamide (10.2 g., 0.083 mole) was added to a mixture of 19 g. (0.083 mole) of 4-(1-tricyclo[3.3.1.1$^{3,7}$]decyl)phenol in 50 ml. of sulfuric acid and 500 ml. of acetic acid. After stirring at room temperature for 3 hours, the mixture was poured into 3 liters of water with stirring. The precipitate was refluxed with 75 ml. of ethanol and 25 ml. of concentrated hydrochloric acid for 3 hours. After cooling −20° C., the precipitate was collected to give 12 g. of 2-aminomethyl-4-[1-tricyclo(3.3.1.1$^{3,7}$)decyl]phenol hydrochloride, m.p. 272°–274° C.

Step B: Preparation of 2-aminomethyl-4-[1-tricyclo(3.3.1.1$^{3,7}$)decyl]-6-iodophenol The amine hydrochloride from Step A (2.93 g., 0.01 mole) was dissolved in 600 ml. of hot water, cooled to 40° C. and 1.64 g. of iodine monochloride in 3N HCl (8 ml) was stirred in rapidly. After stirring 2 hours, the mixture was let stand overnight. After cooling to 0° C., the precipitate was collected and recrystallized from 75 ml. of ethanol and 20 ml. of concentrated hydrochloric acid to give 3.3 g. of 2-aminomethyl-4-[1-tricyclo(3.3.1.1$^{3,7}$)decyl]-6-iodophenol hydrochloride, m.p. 232°–233° C.

This is converted to the free base by solution in 1 l. of water and addition of excess ammonium hydroxide.

Step C: Preparation of 3,4-dihydro-6-[1-tricyclo(3.3.1.1$^{3,7}$)decyl]-8-iodospiro[2H-1,3-benzoxazine-2,2'-tricyclo(3.3.1.1$^{3,7}$)decane]

Employing the procedure substantially as described in Example 3, Step C, but substituting for the 2-aminomethyl-4-(1,1-dimethylethyl)-6-trifluoromethylphenol used therein, an equimolar amount of 2-aminomethyl-4-[1-tricyclo(3.3.1.1$^{3,7}$)decyl]-6-iodophenol, there is produced 3,4-dihydro-6-[1-tricyclo(3.3.1.1$^{3,7}$)decyl]-8-iodospiro-[2H-1,3-benzoxazine-2,2'-tricyclo(3.3.1.1$^{3,7}$)decane].

EXAMPLE 8

3,4-Dihydro-5,7-Dichloro-6,8-dimethylspiro[2H-1,3-benzoxazine-2,2'-tricyclo(3.3.1.1$^{3,7}$)decane]

Step A: Preparation of 2-chloro-N-[2-methoxy-3,5-dimethylphenyl]methyl acetamide To a solution of 2.72 g. (0.02 mole) of 2,4-dimethylanisole in 20 ml. of acetic acid and 2 ml. of sulfuric acid was added (2.47 g., 0.02 mole) 2-chloro-N-(hydroxymethyl)acetamide at < 20° C. over a 10 minute period with stirring. After standing at room temperature about 20 hours the mixture was poured with stirring into 250 ml. of ice-water. After 1 hour the precipitate was collected, washed with water and dried at 60° C. and recrystallized 3 times from methanol:water (3:2), once from ethanol:water (3:2) and twice from ethanol:water (1:1) to give 0.34 g. of 2-chloro-N-[2-methoxy-3,5-dimethylphenyl]methyl acetamide, m.p. 124°–124.5° C.

Step B: Preparation of 2-chloro-N-[2-methoxy-3,5-dimethyl-4,6-dichlorophenyl]methylacetamide A stirred, intimate mixture of 2.42 g. (0.01 mole) of 2-chloro-N-[2-methoxy-3,5-dimethylphenyl]methylacetamide and 1.45 g. (0.011 mole) of aluminum chloride was treated with a mixture of 6 g. (0.044 mole) of sulfuryl chloride and 8 drops of sulfur monochloride. After stirring and heating on a steam bath for 1.5 hours, and cooling, there was added 200 ml. of 10% (v/v) hydrochloric acid. The precipitate was recrystallized 5 times from ethanol/water to give 0.25 g. of 2-chloro-N-[2-methoxy-3,5-dimethyl-4,6-dichlorophenyl]methylacetamide, m.p. 205°–206° C.

Step C: Preparation of 2-aminomethyl-3,5-dichloro-4,6-dimethylphenol

2-Chloro-N-[2-methoxy-3,5-dimethyl-4,6-dichlorophenyl]methylacetamide (1.6 g., 0.00515 mole) was refluxed with 20 ml. of 48% hydrobromic acid, and 20 ml. of acetic acid for 1.5 hours. After cooling to about 5° C., the precipitate was collected, washed with ether, dried at 60° C. to give 1.3 g. of 2-aminomethyl-3,5-dichloro-4,6-dimethylphenol hydrobromide, m.p. 305°–307° C. (dec.).

This material is converted to the free base by dissolving in 75 ml. of water and adding excess ammonium hydroxide.

Step D: Preparation of 3,4-dihydro-5,7-dichloro-6,8-dimethylspiro[2H-1,3-benzoxazine-2,2′-tricyclo(3.3.1.1$^{3,7}$)decane]

Employing the procedure substantially as described in Example 3, Step C, but substituting for the 2-aminomethyl-4-(1,1-dimethylethyl)-6-trifluoromethylphenol used therein, an equimolar amount of 2-aminomethyl-3,5-dichloro-4,6-dimethylphenol, there is produced 3,4-dihydro-5,7-dichloro-6,8-dimethylspiro[2H-1,3-benzoxazine-2,2′-tricyclo(3.3.1.1$^{3,7}$)decane].

EXAMPLE 9

3,4-Dihydro-6-(1,1-dimethylethyl)-8-iodospiro[2H-1,3-benzoxazine-2,1′-cyclohexane]

A mixture of 2-aminomethyl-4-(1,1-dimethylethyl)-6-iodophenol (1.5 g., 0.005 mole), cyclohexanone (0.5 g., 0.005 mole), and magnesium sulfate (0.5 g.) in tetrahydrofurane (50 ml.) is kept under nitrogen at 20°–25° C., for 16 hours. The magnesium sulfate is removed and the filtrate evaporated to dryness. The residue is crystallized from ethanol to obtain 3,4-dihydro-6-(1,1-dimethylethyl)-8-iodospiro[2H-1,3-benzoxazine-2,1′-cyclohexane] (1.4 g.), m.p. 112°–114° C.

If in the above procedure the magnesium sulfate is replaced by an equal weight of molecular sieves, there is obtained 1.4 g. of 3,4-dihydro-6-(1,1-dimethylethyl)-8-iodospiro[2H-1,3-benzoxazine-2,1′-cyclohexane], m.p. 112.5°–114.5° C.

EXAMPLE 10

3,4-Dihydro-6-(1,1-dimethylethyl)-8-iodospiro[2H-1,3-benzoxazine-2,2′-tricyclo(3.3.1.1$^{3,7}$)decane]

A mixture of 2-aminomethyl-4-(1,1-dimethylethyl)-6-iodophenol (1.5 g., 0.005 mole), 2-oxotricyclo(3.3.1.1.$^{3,7}$)-decane (0.75 g., 0.005 mole) and p-toluenesulfonic acid (50 mg.) in benzene (25 ml.) is refluxed under a Dean-Stark trap for 2 hr. The solution is cooled, filtered, and evaporated to dryness. The residue is crystallized from ethanol to obtain 3,4-dihydro-6-(1,1-dimethylethyl)-8-iodospiro[2H-1,3-benzoxazine-2,2′-tricyclo(3.3.1.1$^{3,7}$)decane] (1.4 g.), m.p. 165°–166° C.

If the p-toluene sulfonic acid is omitted from the above reaction, there is obtained 1.8 g. of 3,4-dihydro-6-(1,1-dimethylethyl)-8-iodospiro[2H-1,3-benzoxazine-2,2′-tricyclo(3.3.1.1$^{3,7}$)decane], m.p. 162°–164° C.

If the aminomethylphenol in the above procedure (1.5 g.) and 2-adamantanone (0.75 g.) in dioxane (15 ml.) are refluxed under a Soxhlet extractor, in which the thimble is filled with molecular sieves, for 4 hr. and the mixture worked up in the same manner, there is obtained 3,4-dihydro-6-(1,1-dimethylethyl)-8-iodospiro[2H-1,3-benzoxazine-2,2′-tricyclo(3.3.1.1$^{3,7}$)decane] (1.4 g.), m.p. 162°–164° C.

EXAMPLE 11

3,4-Dihydro-6-chlorospiro[pyrido(3.2.h)-2H-1,3-benzoxazine-2,2′-tricyclo(3.3.1.1$^{3,7}$)decane]

Step A: Preparation of N-(5-chloro-8-hydroxy-6-quinolylmethyl)phthalimide

N-(hydroxymethyl)phthalamide (19 g., 0.107 mole) is added portion-wise (1 hr.) at about 20° to a well stirred solution of 5-chloro-8-hydroyquinoline (18 g., 0.1 mole) in conc. H$_2$SO$_4$ (200 ml.). Stirring at 20° is continued for 2½ hr. and then at 85°–90° for 25 hr. The cooled mixture then is stirred into ice-water, the aqueous mixture is adjusted to pH ca. 5 (NaOH and NaHCO$_3$). The precipitated imide is collected, dried and crystallized from benzene to obtain N-(5-chloro-8-hydroxy-6-quinolylmethylphthalimide, m.p. 245°–247° C.

Step B: Preparation of 5-Chloro-7-aminomethyl-8-hydroxyquinoline dihydrochloride The imide prepared in Step A (34 g., 0.098 mole) is added to 12 N hydrochloric acid (2 l) and the mixture is refluxed for 52 hr. Th cooled mixture is filtered to remove the phthalic acid formed in the hydrolysis, concentrated to a small volume, and diluted with water. Upon neutralization with conc. NH$_4$OH a solid separates. This is crystallized from a mixture of water, ethanol and con. hydrochloric acid to obtain 5-chloro-7-aminomethyl-8-hydroxyquinoline dihydrochloride (15.5 g.), m.p. 237°–241° C. (dec.).

Step C: Preparation of 3,4-Dihydro-6-chlorospiro[pyrido-(3.2.h)-2H-1,3-benzoxazine-2,2′-tricyclo-(3.3.1.1$^{3,7}$)decane]

A mixture of 5-chloro-7-aminomethyl-8-hydroxyquinoline (2.08 g., 0.01 mole), 2-oxotricyclo(3.3.1.1$^{3,7}$)-decane (1.5 g., 0.01 mole) and benzene (100 ml.) is refluxed under a Dean-Stark trap for 4 hrs. The solvent is evaporated and the residue is crystallized from benzene-hexane to obtain 3,4-dihydro-6-chlorospiro[pyrido(3.2.h)-2H-1,3-benzoxazine-2,2′-tricyclo(3.3.1.1$^{3,7}$)decane] (2.3 g.) m.p. 146°–149° C.

EXAMPLE 12

3,4,3″,4″-Tetrahydro-6,6″-bis(1,1-dimethylethyl)-8,8″-diiododispiro[2H-1,3-benzoxazine-2,1′-cyclohexane-4′,2″-2″H-1″,3″-benzoxazine]

A mixture of 2-aminomethyl-4-(1,1-dimethylethyl)-6-iodophenol (3.0 g., 0.01 mole), of 1,4-cyclohexandione (0.36 g., 0.005 mole) and benzene (100 ml.) is refluxed under a Dean-Stark trap for 4 hr. The solvent is evaporated and the residue is crystallized from benzene to obtain 3,4,3″,4″-tetrahydro-6′,6″-bis(1,1-dimethylethyl)-8,8''-diiododispiro[2H-1,3-benzoxazine-2,1'-cyclohexane-4',2''-2''H-1'',3''-benzoxazine] (0.85 g.), m.p. 177°–178° C.

EXAMPLE 13

(1) Tablets — 10,000 scored tablets for oral used, each containing 500 mg. of active ingredient are prepared from the following ingredients:

|  | Gm. |
|---|---|
| 3,4-dihydro-6-(1,1-dimethylethyl)-8-iodospiro[2H-1,3-benzoxazine-2,4'-tetrahydrothiopyran] | 5000 |
| Starch, U.S.P. | 350 |
| Talc, U.S.P. | 250 |
| Calcium stearate | 35 |

The active ingredient is granulated with a 4% w./v. aqueous solution of methylcellulose U.S.P. (1500 cps). To the dried granules is added a mixture of the remainder of the ingredients and the final mixture compressed into tablets of proper weight.

(2) Capsules — 10,000 two-piece hard gelatin capsules for oral use, each containing 250 mg. of active ingredient are prepared from the following ingredients:

|  | Gm. |
|---|---|
| 3,4-dihydro-6-(1,1-dimethylethyl)-8-iodospiro[2H-1,3-benzoxazine-2,1'-cyclohexane | 2500 |
| Lactose, U.S.P. | 1000 |
| Starch, U.S.P. | 300 |
| Talc, U.S.P. | 65 |
| Calcium Stearate | 25 |

The active ingredient is mixed with the starch lactose mixture followed by the talc and calcium stearate. The final mixture is then encapsulated in the usual manner. Capsules containing 10, 25, 50, and 100 mg. of active ingredient are also prepared by substituting 100, 250, 500, and 1000 gm. of 2500 gm. in the above formulation.

(3) Soft elastic capsules — One-piece soft elastic capsules for oral use, each containing 500 mg. of active material are prepared in the usual manner by first dispersing the active material in sufficient corn oil to render the material capsulatable.

(4) Aqueous suspension — An aqueous suspension for oral use containing in each 5 ml., 0.25 g. of active ingredient is prepared from the following ingredients:

|  | Gm. |
|---|---|
| 3,4-dihydro-6-(1,1-dimethylethyl)-8-iodospiro[2H-1,3-benzoxazine-2,1'-cyclohexane | 500 |
| Methylparaben, U.S.P. | 7.5 |
| Propylparaben, U.S.P. | 2.5 |
| Saccharin sodium | 12.5 |
| Glycerin | 3000 |
| Tragacanth powder | 10 |
| Orange oil flavor | 10 |
| F.D.& C. orange dye | 7.5 |
| Deionized water, q.s. to 10,000 ml. |  |

(5) Gel Formulation
0.1 mg. disodium edetate
1.30 mg. of purified H$_2$O
300 mg. isopropanol
26 mg. hydroxypropylcellulose
q.s.a.d. 1 gm. propylene glycol
50 mg. 3,4-dihydro-6-(1,1-dimethylethyl)-8-iodospiro[2H-1,3-benzoxazine-2,1'-cyclohexane (6) Ointment Formulation
50 mg. wool alcohols B.P.
150 mg. amichol C
350 mg. white wax
q.s.a.d. 1 gm. isopropyl myristate
50 mg. 3,4-dihydro-6-(1,1-dimethylethyl)-8-iodospiro[2H-1,3-benzoxazine-2,1'-cyclohexane
0.4% citrate acid anhydrous
0.58% sodium phosphate dibasic anhydrous.

What is claimed is:
1. A compound of formula:

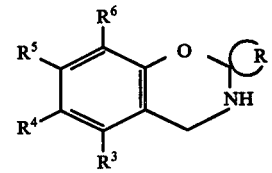

wherein
R$^3$ is
(1) hydrogen,
(2) methyl,
(3) chloro, or
(4) methoxy;
R$^4$ is
(1) halo,
(2) lower alkyl, or
(3) adamantyl;
R$^5$ is
(1) hydrogen,
(2) lower alkyl,
(3) lower alkoxy, or
(4) halo;
R$^6$ is
(1) halo,
(2) lower alkyl,
(3) lower alkylthio, or
(4) trifluoromethyl;
R$^5$ and R$^6$ taken together is —N=CH—CH=CH—, and
R is
(1) a spiro-carbocycle of 5, 6, or 10–17 members, unsubstituted or substituted with
  (a) lower alkyl,
  (b) lower alkoxy,
  (c) phenyl, or
  (d) phenyl substituted with lower alkoxy, or
  (e) lower alkanoyloxy;
(2) a 6-membered spiroheterocycle containing 1 or 2 heteroatoms selected from oxygen, sulfur, and nitrogen wherein the nitrogen heteroatom can be substituted with lower alkyl, phenyl-lower alkyl, or lower alkanoyl;
(3) a spiro-polycycloalkyl of 6–15 members, or

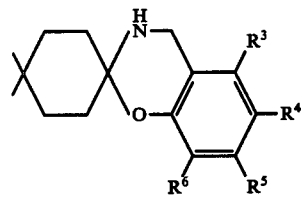
(4)

2. The compound of claim 1 with formula:

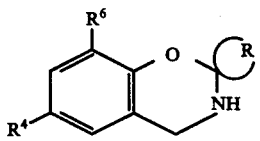

3. The compound of claim 1 with formula:

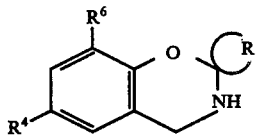

wherein $R^4$ is lower alkyl, $R^6$ is halo.

4. The compound of claim 1 with formula:

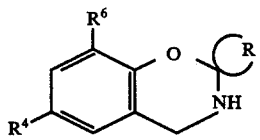

wherein $R^4$ is lower alkyl, $R^6$ is halo and ⌒R is spiro-tetrahydrothiapyran or spirocyclohexane.

5. The compound of claim 1 which is 3,4-dihydro-6-(1,1-dimethylethyl)-8-iodospiro[2H-1,3-benzoxazine-2,1'-cyclohexane].

6. The compound of claim 1 which is 3,4-dihydro-6-(1,1-dimethylethyl)-8-chlorospiro[2H-1,3-benzoxazine-2,1'-cyclohexane].

7. The compound of claim 1 which is 1'-methyl-3,4-dihydro-6-(1,1-dimethylethyl)-8-iodospiro[2H-1,3-benzoxazine-2,4'-piperidine].

8. The compound of claim 1 which is 3,4-dihydro-6-(1,1-dimethylethyl)-8-iodospiro[2H-1,3-benzoxazine-2,3'-tricyclo[2.2.1.0$^{2,6}$]heptane].

9. The compound of claim 1 which is 3,4-dihydro-6-(1,1-dimethylethyl)-8-iodospiro[2H-1,3-benzoxazine-2,2'-tricyclo[3.3.1.1$^{3,7}$]decane].

10. The compound of claim 1 which is 3,4-dihydro-6-(1,1-dimethylethyl)-8-iodospiro[2H-1,3-benzoxazine-2,4'-tetrahydrothiapyran].

11. A method of treating edema, abnormal electrolyte retention and inflammation, which comprises administration to a patient in need of such treatment a therapeutically effective amount of a compound of formula:

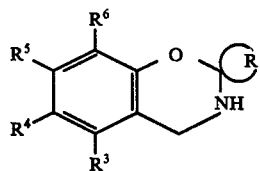

wherein
$R^3$ is
  (1) hydrogen,
  (2) methyl,
  (3) chloro, or
  (4) methoxy;
$R^4$ is
  (1) halo,
  (2) lower alkyl, or
  (3) adamantyl;
$R^5$ is
  (1) hydrogen,
  (2) lower alkyl,
  (3) lower alkoxy, or
  (4) halo;
$R^6$ is
  (1) halo,
  (2) lower alkyl,
  (3) lower alkylthio, or
  (4) trifluoromethyl;
$R^5$ and $R^6$ taken together is —N=CH—CH=CH—, and
R is
  (1) a spiro-carbocycle of 5, 6, or 10–17 members, unsubstituted or substituted with
    (a) lower alkyl,
    (b) lower alkoxy,
    (c) phenyl, or
    (d) phenyl substituted with lower alkoxy, or
    (e) lower alkanoyloxy;
  (2) a 6-membered spiroheterocycle containing 1 or 2 heteroatoms selected from oxygen, sulfur, and nitrogen wherein the nitrogen heteroatom can be substituted with lower alkyl, phenyl-lower alkyl, or lower alkanoyl;
  (3) a spiro-polycycloalkyl of 6–15 members, or

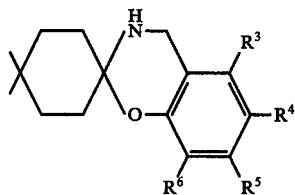

(4)

12. A pharmaceutical composition comprising a pharmaceutically acceptable carrier and a therapeutically effective amount of a compound of formula:

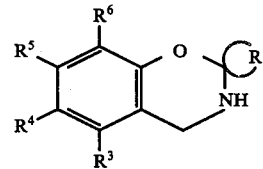

wherein
$R^3$ is
  (1) hydrogen,
  (2) methyl,
  (3) chloro, or
  methoxy;
$R^4$ is
  (1) halo,
  (2) lower alkyl, or
  (3) adamantyl;
$R^5$ is
  (1) hydrogen,
  (2) lower alkyl,
  (3) lower alkoxy, or
  (4) halo;
$R^6$ is
  (1) halo,
  (2) lower alkyl, (3) lower alkylthio, or
(4) trifluoromethyl;

R⁵ and R⁶ taken together is —N=CH—CH=CH—, and

R is
(1) a spiro-carbocycle of 5, 6, or 10–17 members, unsubstituted or substituted with
   (a) lower alkyl,
   (b) lower alkoxy,
   (c) phenyl, or
   (d) phenyl substituted with lower alkoxy, or
   (e) lower alkanoyloxy;
(2) a 6-membered spiroheterocycle containing 1 or 2 heteroatoms selected from oxygen, sulfur, and nitrogen wherein the nitrogen heteroatom can be substituted with lower alkyl, phenyl-lower alkyl, or lower alkanoyl;
(3) a spiro-polycycloalkyl of 6–15 members, or

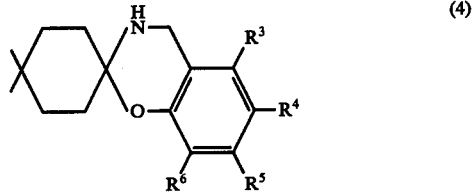

(4)

* * * * *